(12) United States Patent
Shikata et al.

(10) Patent No.: US 11,033,249 B2
(45) Date of Patent: Jun. 15, 2021

(54) EXTERNAL ULTRASONIC PROBE

(71) Applicant: TOSHIBA MEDICAL SYSTEMS CORPORATION, Otawara (JP)

(72) Inventors: Hiroyuki Shikata, Nasushiobara (JP); Yusuke Kobayashi, Kawasaki (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 456 days.

(21) Appl. No.: 15/169,088

(22) Filed: May 31, 2016

(65) Prior Publication Data
US 2017/0000459 A1    Jan. 5, 2017

(30) Foreign Application Priority Data

Jun. 30, 2015 (JP) .............................. JP2015-131601

(51) Int. Cl.
*A61B 8/00* (2006.01)
*B06B 3/00* (2006.01)

(52) U.S. Cl.
CPC .......... *A61B 8/4494* (2013.01); *A61B 8/4281* (2013.01); *A61B 8/4427* (2013.01);
(Continued)

(58) Field of Classification Search
CPC ....... B06B 3/00; A61B 8/4488; A61B 8/4494; A61B 8/4281; A61B 8/4427;
(Continued)

(56) References Cited

U.S. PATENT DOCUMENTS

| | | | | |
|---|---|---|---|---|
| 2,438,936 A | * | 4/1948 | Mason | G10K 11/30 367/150 |
| 4,651,850 A | * | 3/1987 | Matsuo | G10K 11/30 181/175 |

(Continued)

FOREIGN PATENT DOCUMENTS

| | | |
|---|---|---|
| JP | H09-037377 A | 2/1997 |
| JP | 3056624 | 6/2000 |
| JP | 2009-247416 A | 10/2009 |

OTHER PUBLICATIONS

Carovac, Aladin, et al. Application of Ultrasound in Medicine. Acta Inform Med, vol. 19, No. 3, Sep. 2011, pp. 168-171 [online], [retrieved on Oct. 1, 2018]. Retrieved from the Internet: <URL: https://www.ncbi.nlm.nih.gov/pmc/articles/PMC3564184/pdf/AIM-19-168.pdf> <doi: 10.5455/aim.2011.19.168-171 >.*

(Continued)

*Primary Examiner* — Carolyn A Pehlke
*Assistant Examiner* — Victoria Fang
(74) *Attorney, Agent, or Firm* — Oblon, McClelland, Maier & Neustadt, L.L.P.

(57) ABSTRACT

An external ultrasonic probe includes a transducer array including multiple transducers arranged along an azimuth direction, the multiple transducers transmitting and receiving ultrasonic waves; and a covering material having a projecting surface touchable with a living body, formed of a single member, covering an entire front-surface side of the transducer array, and covering at least a part of a side-surface side of the transducer array. In a section dividing a width of the transducer array in the azimuth direction substantially into two equal parts, a width between two points on the projecting surface falling down from a top of the projecting surface by 2 mm is larger than a width of the transducer array in an elevation direction. A difference between the (Continued)

width between the two points and the width of the transducer array in the elevation direction is 5 mm or less.

11 Claims, 7 Drawing Sheets

(52) U.S. Cl.
CPC .............. *A61B 8/4444* (2013.01); *B06B 3/00* (2013.01); *A61B 8/4472* (2013.01)

(58) Field of Classification Search
CPC ... A61B 8/4455; A61B 8/4472; A61B 8/4483; A61B 8/4444
USPC .......................................................... 600/459
See application file for complete search history.

(56) References Cited

U.S. PATENT DOCUMENTS

| | | | | |
|---|---|---|---|---|
| 5,152,294 A * | 10/1992 | Mochizuki | ............... | A61B 8/14 128/916 |
| 6,419,633 B1 * | 7/2002 | Robinson | ................. | A61B 8/14 600/443 |
| 2003/0053915 A1 * | 3/2003 | Keilman | ................. | F04B 17/00 417/322 |
| 2005/0124889 A1 * | 6/2005 | Flesch | ................. | A61B 8/4281 600/445 |
| 2008/0194967 A1 * | 8/2008 | Sliwa | ....................... | A61N 7/02 600/472 |
| 2008/0255456 A1 * | 10/2008 | Kye | ....................... | B06B 1/0622 600/459 |
| 2009/0048521 A1 * | 2/2009 | Hasegawa | ............. | A61B 8/4281 600/459 |
| 2009/0234233 A1 * | 9/2009 | Nagano | ..................... | A61B 8/12 600/462 |
| 2009/0299194 A1 * | 12/2009 | Matsuzawa | ............... | A61B 8/14 600/459 |
| 2010/0256488 A1 * | 10/2010 | Kim | ....................... | B06B 1/0633 600/439 |
| 2011/0224551 A1 * | 9/2011 | Barnard | ................... | A61B 8/08 600/445 |
| 2011/0319768 A1 * | 12/2011 | Saito | ..................... | A61B 8/4281 600/472 |
| 2012/0073376 A1 * | 3/2012 | Naka | ..................... | A61B 8/4461 73/632 |
| 2014/0107492 A1 * | 4/2014 | Zhou | ..................... | G10K 11/357 600/467 |
| 2014/0345385 A1 * | 11/2014 | Irisawa | ................ | A61B 5/0095 73/609 |
| 2015/0071030 A1 * | 3/2015 | Hayashi | .............. | G01S 7/52023 367/7 |
| 2017/0238902 A1 * | 8/2017 | Lee | ....................... | A61B 8/4455 |

OTHER PUBLICATIONS

Office Action dated Feb. 12, 2019 in counterpart Japanese Application No. 2015-131601. Translation retrieved from Global Dossier. Feb. 12, 2019 [retrieved on Aug. 20, 2019].*
Office Action dated Feb. 12, 2019 in counterpart Japanese Application No. 2015-131601.

* cited by examiner

EXTERNAL ULTRASONIC PROBE

CROSS-REFERENCE TO RELATED APPLICATION

This application is based upon and claims the benefit of priority from Japanese Patent Application No. 2015-131601, filed on Jun. 30, 2015, the entire contents of which are incorporated herein by reference.

FIELD

An embodiment as an aspect of the present invention relates to an external ultrasonic probe transmitting and receiving ultrasonic waves.

BACKGROUND

In general, ultrasonic probes used by being connected to an ultrasonic diagnosis apparatus include a one-dimensional array probe (1D probe) in which transducers are arrayed in one direction (azimuth direction), a two-dimensional array probe (2D probe) in which the transducers are arrayed in two directions (azimuth direction and elevation direction) so that an ultrasonic beam can be oscillated electronically in the two directions, and a multiple row array probe (1.5D probe) in which the transducers are arrayed in the two directions but the ultrasonic beam cannot be oscillated in the elevation direction.

In the array-type ultrasonic probes, each of the 1D and 1.5D probes includes an acoustic lens converging the ultrasonic beam along a scan surface and obtaining a thin tomographic surface. The acoustic lens requires use of a material with a sound speed different from those of a body surface and a living body (soft tissue) and with an acoustic impedance close to those of the body surface and the living body. As a material satisfying these requests, silicone rubber which is a material with a sound speed slower than that of the living body or polymethylpentene which is a material with a sound speed faster than that of the living body is known.

When the acoustic lens made of silicone rubber is used, the acoustic lens and a side-surface covering material made of plastic are bonded with a silicone adhesive in general so as to keep water resistance. However, since rigidity of the silicone adhesive itself is low and its adhesion power to the plastic material is also low, a certain adhesion area is required for maintaining reliability. Thus, a width (thickness) of a living-body contact surface of the ultrasonic probe becomes large by the portion of the adhesion area.

When the acoustic lens made of polymethylpentene is used, since a structural body (water bag) for holding an acoustic medium is required, the width of the living-body contact surface of the ultrasonic probe also becomes large.

When a prior-art ultrasonic probe is used to perform ultrasonic imaging from the body surface to an inside of the body (thoracic viscera such as the heart and the liver), since the thoracic viscera are located in a region covered by the costae, intercostal scanning is indispensable. Particularly during scanning under such circumstances that presence of an abnormal region is not known such as during the ultrasonic imaging of the liver, a blind angle in the region behind the costae results in oversight of abnormality.

In order to scan the back of the costae by using the prior-art ultrasonic probe, an operator performs an operation of placing the ultrasonic probe on the intercostal space from the body surface and of tilting the ultrasonic probe. However, if the width of the living-body contact surface of the ultrasonic probe is large, when the operator tilts the ultrasonic probe by a larger angle, an imaging area shifts from the intercostal space. The operation of imaging the intercostal space while largely tilting the ultrasonic probe is impossible, and a blind angle is generated on the back of the costae. In addition, if the operator tries to perform ultrasonic imaging by deeply pressing the ultrasonic probe onto a patient in order to narrow the blind angle, a burden on the patient on whom the ultrasonic probe is pressed becomes large.

The silicone rubber which is the material of the acoustic lens is flexible, and if the ultrasonic probe is erroneously dropped on a floor surface or hit by another device, propagation of an impact on the acoustic lens to the transducers causes a failure of the transducers.

A problem to be solved by the present invention is to provide an external ultrasonic probe which improves operability of the ultrasonic probe by the operator and alleviates the burden of the patient on whom the ultrasonic probe is pressed.

BRIEF DESCRIPTION OF THE DRAWINGS

In accompanying drawings.

DETAILED DESCRIPTION

An external ultrasonic probe according to a present embodiment will be described by referring to the attached drawings.

The external ultrasonic probe according to the present embodiment includes: a transducer array including multiple transducers arranged along an azimuth direction, the multiple transducers transmitting and receiving ultrasonic waves; and a covering material having a projecting surface touchable with a living body, formed of a single member, covering an entire front-surface side of the transducer array, and covering at least a part of a side-surface side of the transducer array. In a section dividing a width of the transducer array in the azimuth direction substantially into two equal parts, a width between two points on the projecting surface falling down from a top of the projecting surface by 2 mm is larger than a width of the transducer array in an elevation direction. A difference between the width between the two points and the width of the transducer array in the elevation direction is 5 mm or less.

Figure 1:
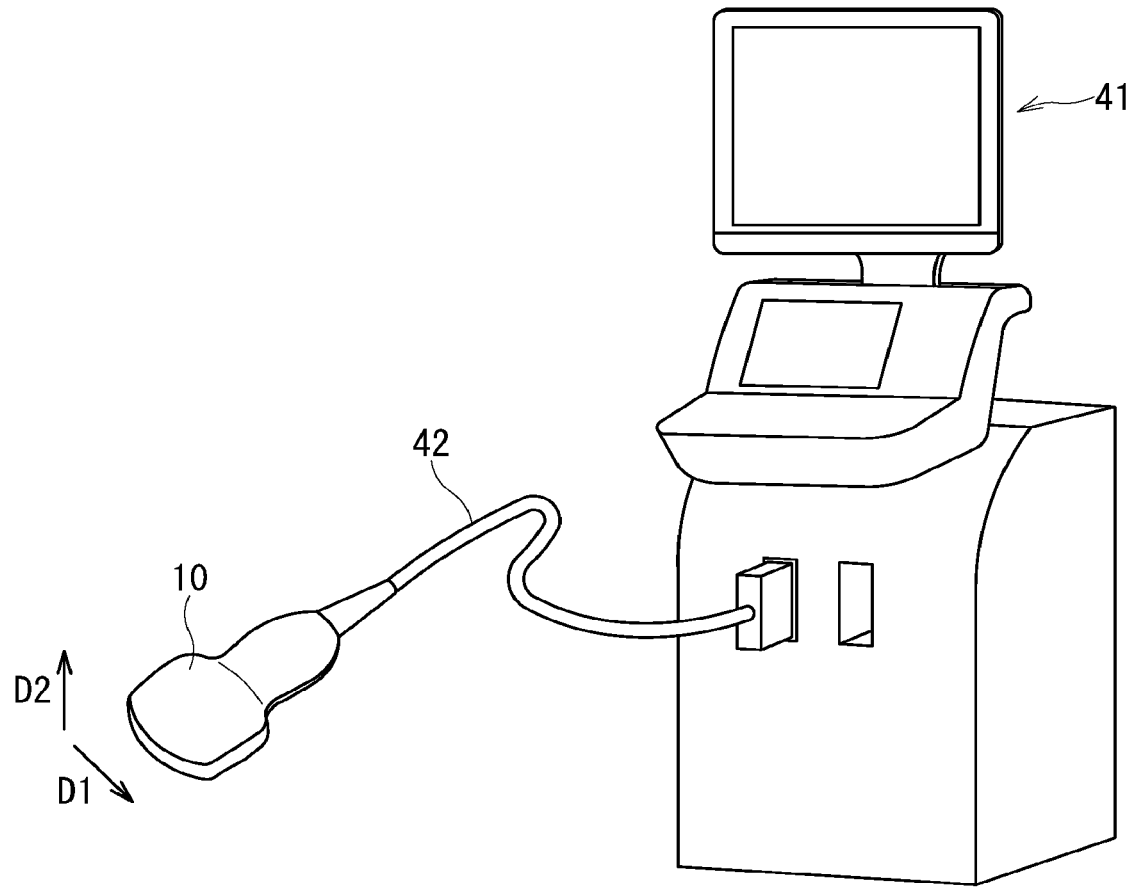
FIG. 1 is a schematic view illustrating configurations of an external ultrasonic probe according to a present embodiment and an ultrasonic diagnosis apparatus.

FIG. 1 is a schematic view illustrating configurations of the external ultrasonic probe according to the present embodiment and an ultrasonic diagnosis apparatus.

FIG. 1 illustrates the external ultrasonic probe (body surface probe) 10 according to the present embodiment and the ultrasonic diagnosis apparatus 41. These may be called the ultrasonic diagnosis apparatus together with the external ultrasonic probe 10 in some cases.

The external ultrasonic probe 10 is used when it approaches from the body surface and images a form of an internal organ or the like. Hereinafter, the external ultrasonic probe is referred to simply as a "probe".

Figure 5:
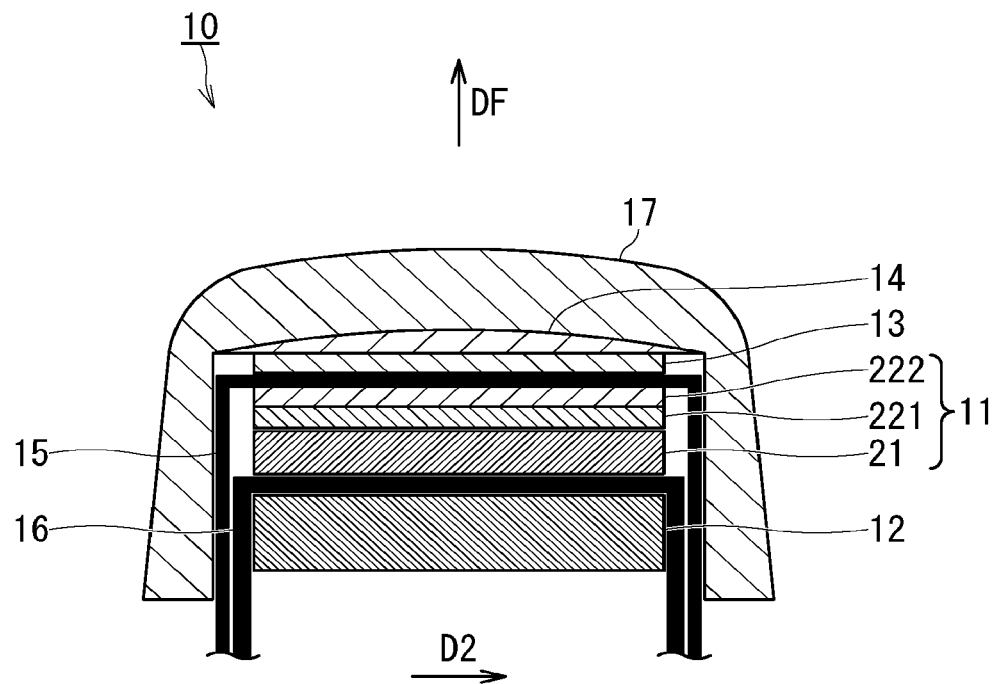
FIG. 5 is a sectional view illustrating a first structure of the tip end portion of the probe according to the present embodiment.

The probe 10 transmits ultrasonic waves to a living body and receives ultrasonic waves from the living body in accordance with control by the ultrasonic diagnosis apparatus 41. The probe 10 includes transducers 11, a backing material 12, a covering material 17 and the like as illustrated in FIG. 5. The transducers 11 include piezoelectric elements 21, first acoustic matching layers 221 and second acoustic matching layers 222 as illustrated in FIG. 5. The transducers 11 does not have to include all of the components above except the piezoelectric elements 21, and the configuration of a hard back layer and the like, not shown, located between the piezoelectric elements 21 and the backing material 12 may be additionally provided, for example. Each of the piezoelectric elements 21 included in the transducers 11 of the probe 10 is an electroacoustic conversion element and has a function of converting an electric signal to ultrasonic waves (transmitted ultrasonic waves) during transmission and of converting ultrasonic reflection waves (received ultrasonic waves) to the electric signal (received signal) during reception.

The transducers 11 are one-dimensionally arrayed along a first direction (azimuth direction) D1 and form a transducer array. In this case, the probe 10 is a 1D probe.

Alternatively, the transducers 11 are two-dimensionally arrayed along the first direction D1 and a second direction (elevation direction) D2 and form a transducer array. In this case, the probe 10 in the present embodiment is a 1.5D probe that cannot oscillate the ultrasonic beam in the second direction.

The probe 10 has a small size and a light weight and is connected to the ultrasonic diagnosis apparatus 41 via a cable 42. The probe 10 is of a sector scanning type, a linear scanning type or a convex scanning type, and any one of them is selected arbitrarily in accordance with a region to be diagnosed. A specific structure of the probe 10 will be described later by using FIGS. 5 and 7. The probe 10 may output a signal to the ultrasonic diagnosis apparatus 41 by using wireless communication.

The ultrasonic diagnosis apparatus 41 controls an operation of the probe 10 and transmits a driving pulse for driving the piezoelectric elements 21 of the probe 10 to the probe 10. The ultrasonic diagnosis apparatus 41 controls the operation of the probe 10 and receives an electric received signal converted by the piezoelectric elements 21 of the probe 10 and generates an ultrasonic image such as a B-mode image.

Subsequently, the prior-art probe will be described by using FIGS. 2 to 4.

Figure 2:
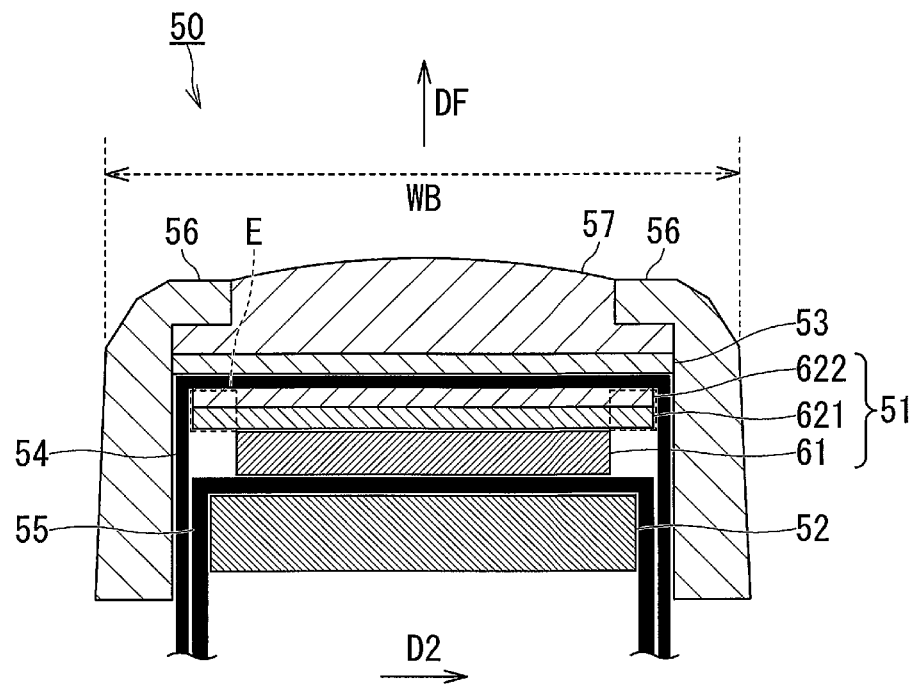
FIG. 2 is a sectional view illustrating a structure of a tip end portion of a prior-art probe.
Figure 3:
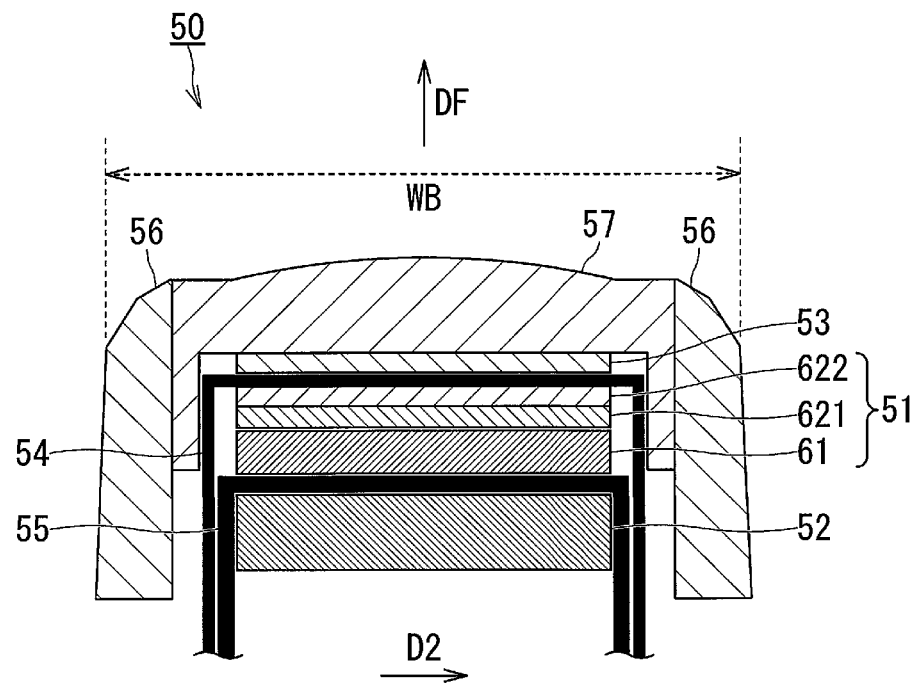
FIG. 3 is a sectional view illustrating a structure of a tip end portion of a prior-art probe.

Each of FIGS. 2 and 3 is a sectional view illustrating a structure of a tip end portion of a prior-art probe. Specifically, they are sectional views of a section dividing a width of the transducer array of a probe 50 in the first direction (azimuth direction) substantially into two equal parts.

The probe 50 includes transducers 51, a backing material 52, a third acoustic matching layer 53, a ground (GND) lead 54, a signal line 55, a side-surface covering material 56, and an acoustic lens 57.

The transducers 51 include piezoelectric elements 61, a first acoustic matching layer 621, and a second acoustic matching layer 622.

The side-surface covering material 56 is made of plastic and covers a side-surface side of the transducers 51.

The acoustic lens 57 is made of silicone rubber and has a projecting surface touchable with a living body. The acoustic lens 57 contributes to convergence relating to the second direction (elevation direction) D2 of the ultrasonic waves generated by the transducers 51. The acoustic lens 57 covers most of or the whole of the front-surface side of the transducers 51.

The side-surface covering material 56 and the acoustic lens 57 are bonded together with a silicone adhesive in general so as to keep water resistance. However, since rigidity of the silicone adhesive is low and the adhesion power of the silicone adhesive to the plastic material is also low, a somewhat large adhesion area is required for firm adhesion between the side-surface covering material 56 and the acoustic lens 57.

Thus, the adhesion area between the side-surface covering material 56 and the acoustic lens 57 is ensured by two kinds of methods as illustrated in FIGS. 2 and 3. FIG. 2 illustrates a method in which a flat acoustic invalid portion E is provided on the front-surface side of the piezoelectric elements 61, and the side-surface covering material 56 is extended to the front-surface side so as to cover the acoustic invalid portion E, and the side-surface covering material 56 is bonded to the acoustic lens 57. On the other hand, FIG. 3 illustrates a method in which the acoustic lens 57 is extended to a side-surface side of the transducers 51, and the side-surface covering material 56 is bonded to the acoustic lens 57 on the side surface of the acoustic lens 57.

In the method illustrated in FIG. 2, the acoustic invalid portion E is present on the front-surface side of the piezoelectric elements 61. In the method illustrated in FIG. 3, the extended portion of the acoustic lens 57 increases an outer diameter width. In either cases, a width (width of a living-body contact surface) WB of the probe 50 in the second direction D2 on an outer surface on the front-surface side becomes larger than necessary with respect to an effective diameter (acoustically effective diameter) in the second direction D2.

If the probe 50 is used, the width WB of the living-body contact surface of the probe 50 becomes larger than necessary, which causes a failure of the ultrasonic imaging using the probe 50. When the ultrasonic imaging is performed from the body surface to an inside of the body (thoracic viscera such as the heart and the liver), for example, since the thoracic viscera are located in a region covered by the costae, intercostal scanning is indispensable. When the operator is to perform ultrasonic imaging of the back of the costae by largely tilting the probe 50, if the width WB of the living-body contact surface of the probe 50 is large, a part of the imaging area of the probe 50 shifts from the intercostal space and can easily cover the costae. Particularly under such circumstances that presence of an abnormal region is not sure during the ultrasonic imaging of the liver, covering of the costae by a part of the imaging area of the probe 50 results in oversight of abnormality behind the costae. Moreover, the probe 50 is deeply pressed on the body surface, and the burden of the patient on whom the probe 50 is pressed becomes large.

Figure 4:
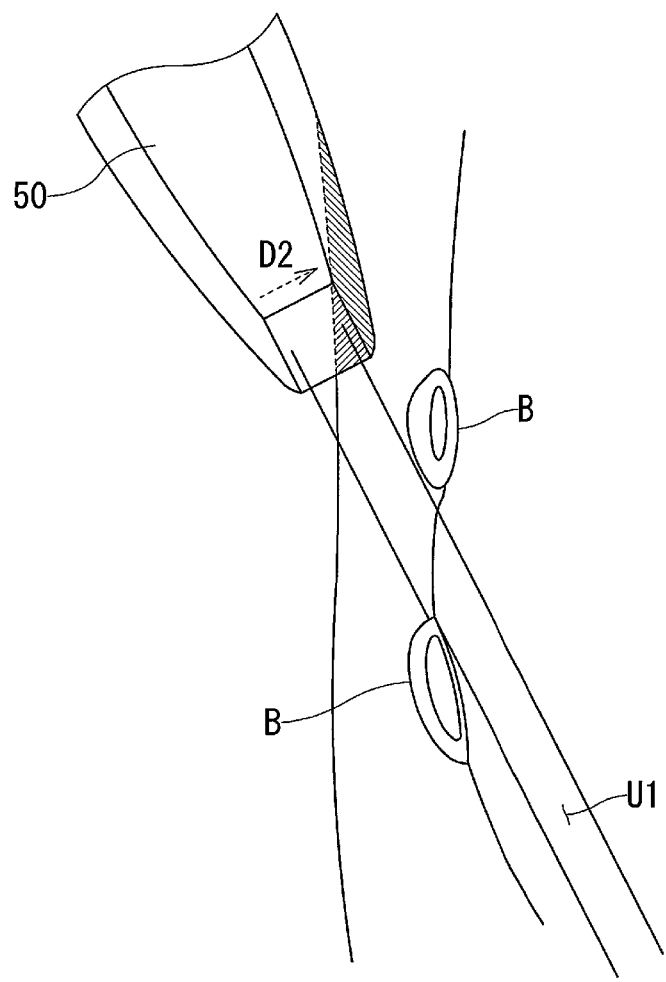
FIG. 4 is a view illustrating the prior-art probe when an ultrasonic imaging of the thoracic viscera is performed.

FIG. 4 is a view illustrating the prior-art probe when the ultrasonic imaging of the thoracic viscera is performed.

As illustrated in FIG. 4, in order to perform the ultrasonic imaging of the living body by using the probe 50, the operator performs an operation of placing the probe 50 on the body surface and of tilting the probe 50 so as to image the living body from between the costae B (intercostal space). Since the width WB (illustrated in FIGS. 2 and 3) of the living-body contact surface of the probe 50 is large, if the operator largely tilts the probe 50 in order to image the back of the costae, a part of an imaging area U1 of the probe 50 shifts from the intercostal space and can cover the costae B easily, which results in easy generation of a blind angle. Moreover, the probe 50 is deeply pressed onto the body surface in order to narrow the contact portion with the body surface (shaded portion illustrated in FIG. 4), and the burden of the patient on whom the probe 50 is pressed becomes large.

Accordingly, reduction of the width WB (illustrated in FIGS. 2 and 3) of the living-body contact surface is required in the probe 50. In order to reduce the width WB of the living-body contact surface of the probe 50, the effective diameter in the second direction D2 needs to be reduced. However, if the effective diameter in the second direction D2 is decreased, it results in deterioration of an image quality at a region (deep region) away from the probe 50 or lowering of a S/N (signal to noise) ratio and thus, a new problem occurs that the whole liver cannot be inspected.

As the prior-art technology, polymethylpentene is used for the acoustic lens, and a probe immersed in an acoustic medium is also present. Polymethylpentene has an acoustic impedance at approximately 1.6 MRayl, which is close to the acoustic impedance of water substantially close to the living body at approximately 1.55 MRayl, and its acoustic matching properties with the living body (water) are favorable. However, polymethylpentene has a sound speed at approximately 2000 m/sec and it is faster than the sound speed of water at approximately 1550 m/sec and in order to obtain a convergence effect of the ultrasonic beam, the living-body contact surface of the acoustic lens 57 (illustrated in FIGS. 2 and 3) including a recessed surface touchable with the living body needs to be provided. If the outer surface of the acoustic lens 57 on the front-surface side is the recessed surface, the lens surface is not brought into close contact with the body surface of the patient during the ultrasonic imaging, and propagation of the sound waves is inhibited. Therefore, when the probe of polymethylpentene is used, a structural body (water bag) for holding the acoustic medium is provided in some cases, but in that case, the width of the living-body contact surface of the probe also becomes large.

Therefore, a design of the probe for reducing the width WB of the living-body contact surface of the probe 50 while the image quality at the deep portion and the S/N ratio are maintained is in high demand.

In addition, since the silicone rubber which is the material of the acoustic lens 57 is flexible, it causes a failure of the transducers 51 by propagation of the impact on the acoustic lens 57 to the transducers 51 when the probe 50 is erroneously dropped on the floor surface or hit by another device. Therefore, the design of the probe which suppresses propagation of the impact on the acoustic lens 57 to the transducers 51 is in high demand.

Subsequently, the probe 10 according to the present embodiment will be described by using FIGS. 5 to 9.

FIG. 5 is a sectional view illustrating a first structure of the tip end portion of the probe 10 according to the present embodiment. Specifically, it is a sectional view of a section dividing the width of the transducer array of the probe 10 in the first direction D1 (illustrated in FIG. 1) substantially into two equal parts.

The probe 10 includes the transducers 11, the backing material 12, a third acoustic matching layer 13, a filling layer 14, a ground (GND) lead 15, a signal line 16, and the covering material 17.

The transducers 11 include the corresponding piezoelectric elements 21, the corresponding first acoustic matching layers 221, and the corresponding second acoustic matching layers 222, for example. The probe 10 in the present embodiment is a 1D probe of a convex type for abdomen. The convex-type 1D probe for abdomen is used for ultrasonic imaging of thoracic viscera such as the heart and the liver and is particularly effective when scanning of the whole liver is needed.

The convex-type 1D probe for abdomen in the present embodiment is capable of transmission of ultrasonic waves with a central frequency at approximately 3 to 5 MHz, for example. An effective diameter WT (illustrated in FIG. 7) of the second direction (elevation direction) D2 in the convex-type 1D probe for abdomen is approximately 6 to 12 mm. The probe 10 in the present embodiment includes only the transducer array having acoustically effective transducers and thus, the effective diameter WT matches a width of all the transducers in the second direction. That is, if the probe 10 is the 1D probe, the effective diameter WT matches the width of a single transducer in the second direction.

The acoustic matching layers 221 and 222 are provided in a front surface direction DF of the piezoelectric elements 21 and are intermediate substances provided in order to reduce a difference in acoustic impedances between the piezoelectric elements 21 and the living body.

The backing material 12 is provided on a back-surface side (side opposite to the front surface direction DF) of the transducers 11 and generates short pulse waves by suppressing resonance of the piezoelectric elements 21 and also absorbs/attenuates unnecessary ultrasonic waves generated on the back-surface side of the piezoelectric elements 21.

The third acoustic matching layer 13 is provided in the front surface direction DF of the transducers 11 and is an intermediate substance provided in order to reduce the difference in the acoustic impedance between the piezoelectric elements 21 and the living body similarly to the acoustic matching layers 221 and 222.

The filling layer 14 has a projecting surface on the front-surface side, and the projecting surface is in contact with the covering material 17. The filling layer 14 contributes to convergence relating to the second direction D2 of the ultrasonic waves generated in the transducers 11.

The covering material 17 has a projecting surface touchable with the living body, is formed of a single member, and covers the entire front-surface side and at least a part of the side-surface side of the transducers 11. For the covering material 17, a synthetic resin such as polymethylpentene, for example, having been used for the acoustic lens in some probes is used as the material. Polymethylpentene has a favorable acoustic matching property with the living body (water) as described above.

Figure 7:
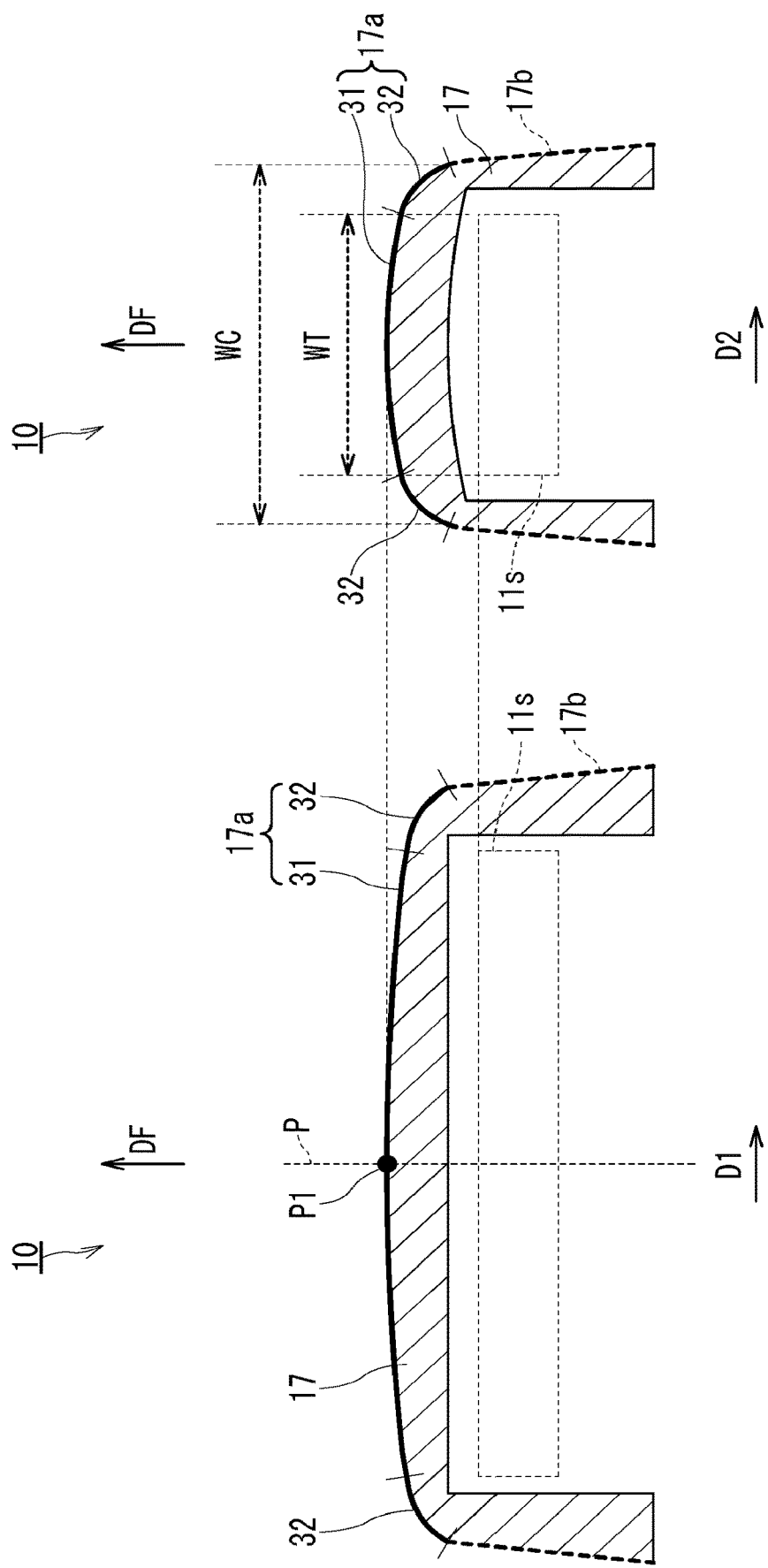
FIG. 7 is a sectional view illustrating a structure of a covering material of the probe according to the present embodiment.

The covering material 17 preferably has an inner surface having a recessed surface shape opposite to the projecting surface (living-body contact surface) touchable with the living body (illustrated in FIG. 7). In that case, radiuses of curvature of the both surfaces do not necessarily have to match each other. In a gap generated between the recessed surface of the covering material 17 and a flat surface on the front surface of the transducers 11, the filling layer 14 is formed. The filling layer 14 is a material having a sound speed slower than that of the acoustic lens 57 (FIGS. 2 and 3) and an acoustic impedance matching that of the lens material, for example.

Specifically, the filling layer 14 is a silicone adhesive whose specific gravity is adjusted by mixing a filler such as silica and is an adhesive used for bonding the covering material 17 and the third acoustic matching layer 13 to each other. Since the living-body contact surface (illustrated in FIG. 7) of the covering material 17 and the inner surface opposite to that are curved in a same direction, there is very little lens effect by the covering material 17, but a convergence effect of the ultrasonic beam can be obtained by a sound speed difference between the filling layer 14 and the living body.

In the covering material 17, the shape of the inner surface opposite to the projecting surface may be other than the recessed surface. The shape of the inner surface of the covering material 17 is a flat surface, for example.

Figure 6:
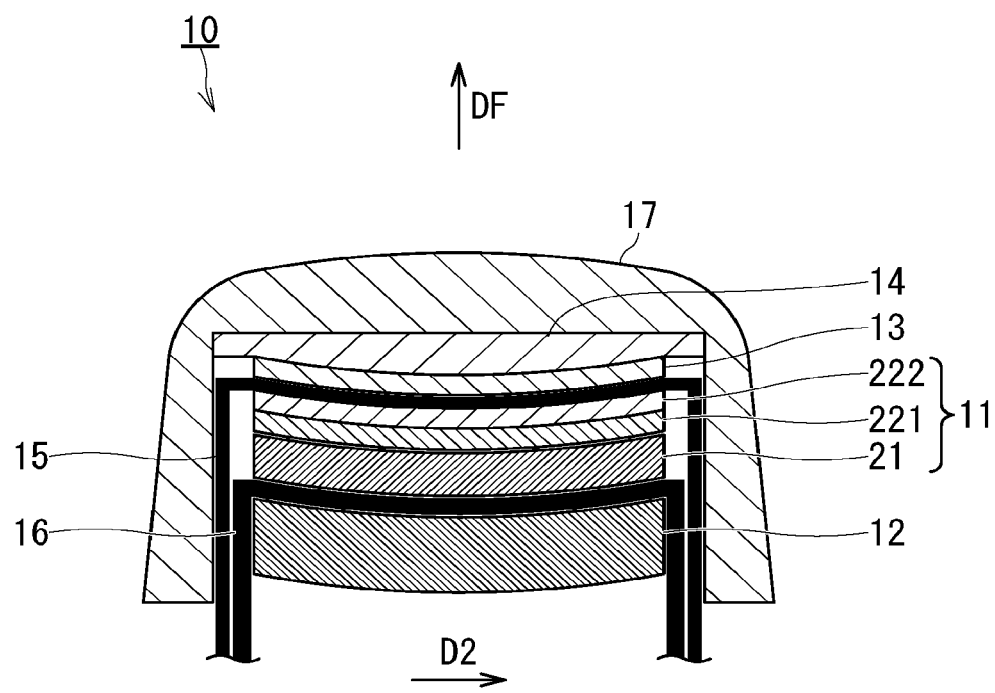
FIG. 6 is a sectional view illustrating a second structure of the tip end portion of the probe according to the present embodiment.

FIG. 6 is a sectional view illustrating a second structure of the tip end portion of the probe 10 according to the present embodiment. Specifically, it is a sectional view of a section dividing the width in the first direction D1 (illustrated in FIG. 1) of the transducer array of the probe 10 substantially into two equal parts.

The probe 10 includes the transducers 11 included in a transducer array with a recessed surface, the backing material 12 with a recessed surface, the third acoustic matching layer 13 with a recessed surface, the filling layer 14, the ground lead 15, the signal line 16, and the covering material 17.

The shape of the inner surface of the covering material 17 is a flat surface. The filling layer 14 is formed in the gap generated between the flat surface of the covering material 17 and the front surface of the recessed surface transducer array. The filling layer 14 is a material having a sound speed slower than that of the acoustic lens 57 (FIGS. 2 and 3) and an acoustic impedance matching that of the lens material, for example.

Specifically, the filling layer 14 is a silicone adhesive whose specific gravity is adjusted by mixing the filler such as silica and is an adhesive used for bonding the covering material 17 and the recessed surface third acoustic matching layer 13 to each other. The convergence effect of the ultrasonic beam can be obtained by the recessed surface transducer array, and a sound speed difference between the filling layer 14 with the slower sound speed and the covering material 17 with the faster sound speed.

Subsequently, the shape of the covering material 17 will be described by using FIGS. 7 and 8.

FIG. 7 is a sectional view illustrating a structure of the covering material 17 of the probe 10 according to the present embodiment. In FIG. 7, the structure of the covering material 17 of the probe 10 according to the present embodiment illustrated in FIG. 5 is exemplified.

The left side in FIG. 7 is a sectional view of a section dividing the width of a transducer array 11s in the second direction D2 substantially into two equal parts. The right side in FIG. 7 is a sectional view of a section dividing a width of the transducer array 11s in the first direction D1 substantially into two equal parts.

In the section illustrated on the right side in FIG. 7, the projecting surface of the covering material 17 touchable with the living body has a first surface 17a (bold solid line) and a second surface 17b (bold broken line). The first surface 17a has a center surface 31 (a surface of the first surface 17a except a round surface 32) located at the center of the projecting surface and the round surfaces 32 located on both ends of the center surface 31. In a section P (illustrated on the left side in FIG. 7) dividing the width of the transducer array 11s in the first direction D1 substantially into two equal parts, the center surface 31 has a first radius of curvature, and the round surface 32 has a second radius of curvature. The second surface 17b is a surface on a side-surface side of at least a part of the transducer array 11s. That is, a connecting surface between the projecting surface center surface 31 and the second curved surface 17b is formed by round processing.

In the section illustrated on the right side in FIG. 7, the radius of curvature (R) of the round surface 32 on the living-body contact surface is preferably approximately 2 mm. If the radius of curvature of the round surface 32 is too small, it gives a pain to the patient when the probe 10 is tilted during the ultrasonic imaging. On the other hand, if the radius of curvature of the round surface 32 is too large, a width WC of the living-body contact surface in the second direction D2 becomes unnecessarily larger than the effective diameter (width of the transducer array 11s in the second direction) WT in the second direction.

Thus, in the present embodiment, in the section dividing the width of the transducer array 11s in the first direction D1 substantially into two equal parts, a width WD (illustrated in FIG. 8) between two points on the projecting surface falling down from the top of the projecting surface by 2 mm is specified.

Figure 8:
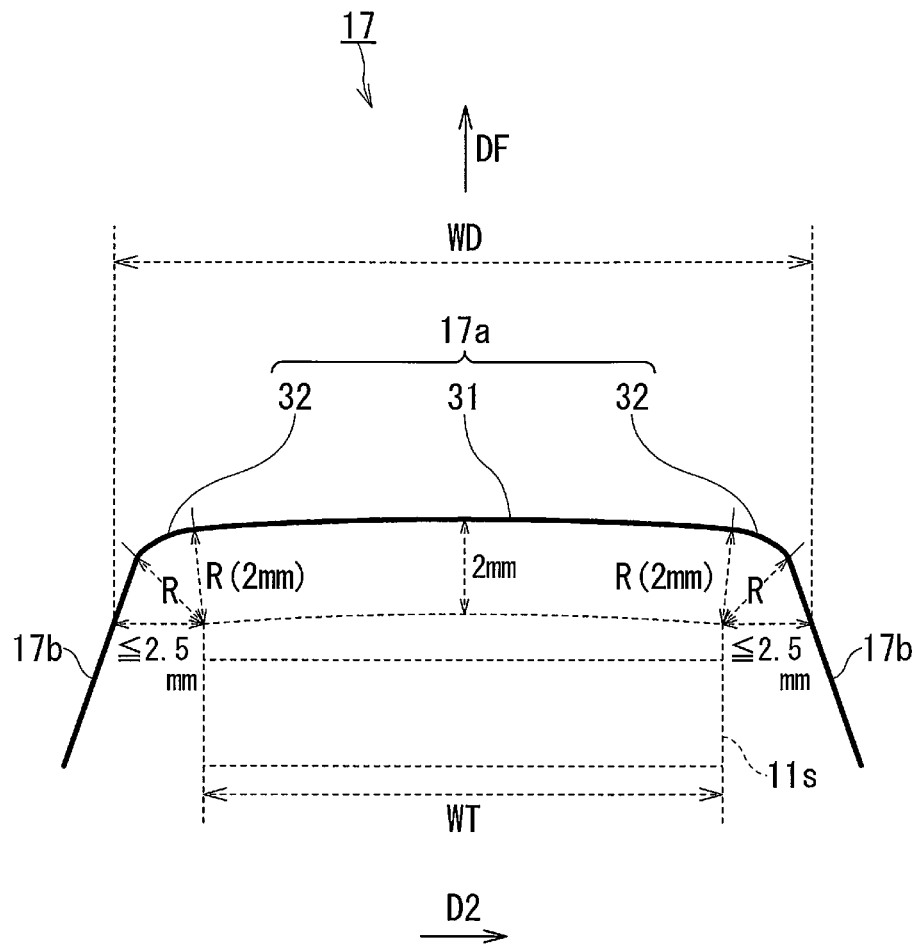
FIG. 8 is a view for explaining a relation between a width between two points on a projecting surface of the covering material and an effective diameter.

FIG. 8 is a view for explaining a relation between the width WD between the two points on the projecting surface of the covering material 17 and the effective diameter WT.

FIG. 8 is a view of the first and second surfaces of the covering material 17 on the section dividing the width of the transducer array 11s in the first direction D1 substantially into two equal parts when seen from the first direction. As illustrated in FIG. 8, the projecting surface of the covering material 17 includes the center surface 31 which is a gently curved surface and the round surface 32 having the radius of curvature of 2 mm.

Since the center surface 31 is the gently curved surface, a direction from a contact point between the center surface 31 and the round surface 32 to the curvature center (center of a circle of curvature) of the round surface 32 can be considered to be substantially parallel with the direction falling down from the top of the projecting surface by 2 mm. Accordingly, if an angle formed by two straight lines between two edges and the curvature center of one side of the round surface 32 is a right angle, though not shown, a difference (WD−WT>0 mm) between the width WD between the two points on the projecting surface falling down from the top of the projecting surface by 2 mm and the width of the transducer array 11s (effective diameter WT) in the second direction D2 is 4 mm, and a difference on the one side is 2 mm which is the same as the radius of curvature of the round surface 32.

However, in actuality, as illustrated in FIG. 8, the both second surfaces 17b have a structure in which the width of the second direction D2 increases toward the back-surface side instead of the structure of being parallel with each other, and thus, the angle formed by the radius of curvature of the round surface 32 is a sharp angle. As the angle formed by the radius of curvature of the round surface 32 become smaller, the difference between the width WD and the width of the transducer array 11s in the second direction D2 is set exceeding 4 mm.

In the covering material 17 has the width WD larger than the effective diameter WT as illustrated in FIG. 8 in order to obtain an angle formed by the radius of curvature of the round surface 32 taking into consideration of contact properties to the body surface of a patient O, the covering material 17 is constituted such that the difference (WD−WT>0 mm) between the width WD and the effective diameter WT in the second direction D2 becomes 5 mm or less. The difference on the one side between the width WD and the effective diameter WT is preferably set to approximately 2.5 mm at the maximum.

By employing the covering material 17 integrally covering the entire front-surface side and at least a part of the side-surface side for the probe 10, the structure in which the difference between the width WD and the effective diameter WT is 5 mm or less can be realized without decreasing the effective diameter WT of the second direction D2. On the other hand, in the prior-art probe 50 illustrated in FIGS. 2 and 3, the structure in which the difference between the width WD and the effective diameter WT is 5 mm or less cannot be realized without decreasing the effective diameter WT of the second direction D2. That is because a certain adhesion area is required between the side-surface covering material 56 of the transducers 51 and the acoustic lens 57 on the front-surface side of the transducers 51 illustrated in FIGS. 2 and 3.

Here, if a thickness of the tip end portion of the covering material 17 in the front surface direction DF is too small, strength is insufficient, a failure such as a crack occurs at a drop impact, and molding of polymethylpentene is difficult. On the other hand, if the thickness of the covering material 17 in the front surface direction DF is too large, attenuation of the ultrasonic waves becomes large, which results in lowered sensitivity, and an influence of refraction caused by a difference in the sound speed from the living body becomes large. Since an attenuation factor of the covering material 17 is substantially in proportion to the frequency, the thickness of the covering material 17 in the front surface direction DF is preferably specified by a relative value to a wavelength in the covering material 17, which is 1.5 to 3 times the wavelength.

The covering material 17 may be constituted such that the effective diameter WT of the second direction D2 is smaller than the effective diameter of the prior-art probe 50 (illustrated in FIGS. 2 and 3) or 6 to 12 mm, for example. By making the effective diameter small, the width of the center surface 31 in the second direction D2 can be made small, and thus, improvement of operability can be made further effective. If the effective diameter WT is decreased as described above, the image quality at the deep portion or the S/N ratio based on the lowering of directivity is expected to be lowered. However, since the lowering of the image quality at the deep portion or the S/N ratio is compensated for by the difference in the attenuation factors between the covering material 17 (polymethylpentene) and the filling layer 14 (silicone rubber), if the effective diameter WT is 6 mm, the image quality and the S/N ratio that can be used substantially without a problem for general imaging of the abdomen can be maintained.

In order to obtain a higher image quality, the 1.5D probe can be used in which the piezoelectric elements 21 are arrayed also in the second direction D2, and diameter switching and independent delay or gain control are executed. In the 1.5D probe, by optimizing the image quality at the deep portion while the optimal maximum effective diameter of 6 to 12 mm is kept, improvement of operability of the probe 10 can be maximized.

Figure 9:
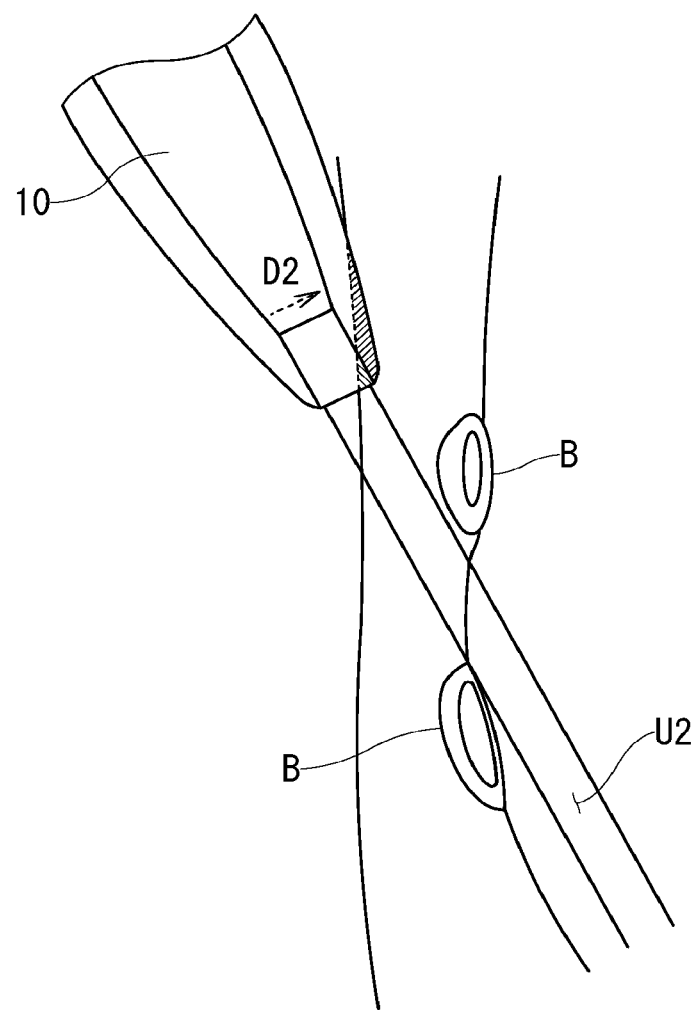
FIG. 9 is a view illustrating the probe when the ultrasonic imaging of the thoracic viscera is performed.

FIG. 9 is a view illustrating the probe 10 when the ultrasonic imaging of the thoracic viscera is performed.

As illustrated in FIG. 9, for the ultrasonic imaging of a living body by using the probe 10, the operator performs the operation of placing the probe 10 on the body surface and of tilting the probe 10 in order to image the living body from between the costae B (intercostal space). Since the width WC of the living-body contact surface (illustrated in FIG. 7) is smaller than the width WB of the prior-art living-body contact surface (illustrated in FIGS. 2 and 3), even if the operator largely tilts the probe 10 in order to image the back of the costae, an imaging area U2 of the probe 10 shifts from the intercostal space and cannot easily cover the costae B, which makes it difficult to generate a blind angle. Moreover, even if the probe 10 is deeply pressed onto the body surface in order to narrow the contact portion with the body surface (shaded portion illustrated in FIG. 9), the burden of the patient on whom the probe 10 is pressed becomes smaller than that of the prior-art one.

In the case that the radius of curvature of the round surface 32 on the living-body contact surface is 2 mm, the structure of the probe 10 in which the difference between the width WD and the effective diameter WT in the second direction D2 (WD−WT>0 mm) is 5 mm or less has been described, but the case is not limiting. For example, the radius of curvature of the round surface 32 of the living-body contact surface may be other than 2 mm. Alternatively, the center surface 31 and the round surface 32 of the living-body contact surface may be a surface formed by a continuous spline curve.

According to the external ultrasonic probe 10 according to the present embodiment, the width WC of the living-body contact surface can be reduced while the image quality at the deep portion and the S/N ratio are maintained. As a result, operability of the probe 10 by the operator is improved, and the burden of the patient on whom the probe 10 is pressed is alleviated.

According to the external ultrasonic probe 10 according to the present embodiment, propagation of an impact to the transducers 11 is suppressed. As a result, risk of a failure caused by the impact on the transducers 11 of the probe 10 is reduced.

According to at least one of the embodiments described above, operability of the ultrasonic probe by the operator can be improved, and the burden of the patient on whom the ultrasonic probe is pressed can be alleviated.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. An external ultrasonic probe comprising:
 a transducer array including multiple transducers arranged along a first direction, the multiple transducers configured to transmit and receive ultrasonic waves from a surface formed by the first direction and a second direction; and
 a covering material having a projecting surface touchable with a living body, formed of a single member, covering an entire front-surface side of the transducer array, and covering at least a part of a side-surface side of the transducer array, wherein a width between two points on the projecting surface along the second direction at a center slice in the first direction is larger than a width of the transducer array in the second direction, each of the two points intersecting the projecting surface and an imaginary line that is depressed by 2 mm from a top of the projecting surface; and a difference between the width between the two points and the width of the transducer array in the second direction is 5 mm or less, wherein the projecting surface of the covering material has, in the center slice, an integral first surface and second surfaces that are arranged at both ends of the first surface, wherein the first surface has a center surface arranged at a center of the projecting surface and round surfaces at both ends thereof, the center surface and the round surfaces having different curvatures, and wherein the first surface and the second surfaces are contiguous and together form a convex curve.

2. The external ultrasonic probe according to claim 1, wherein the width of the transducer array in the second direction is configured to be 6 to 12 mm.

3. The external ultrasonic probe according to claim 1, wherein the covering material is made of a synthetic resin as a material.

4. The external ultrasonic probe according to claim 3, wherein the covering material is made of polymethylpentene as the synthetic resin.

5. The external ultrasonic probe according to claim 1, wherein an inner surface opposite to an outer surface which is the projecting surface in the covering material has a recessed surface.

6. The external ultrasonic probe according to claim 1, wherein a filling material different from the covering material is filled between the covering material and the transducer array; and the filling material is made of a material whose sound speed is slower than that of the covering material.

7. The external ultrasonic probe according to claim 6, wherein the filling material is made of silicone as the material.

8. The external ultrasonic probe according to claim 1, wherein the covering material has a part of the projecting surface to be an arc surface; and a width of the arc surface in the second direction matches an acoustic effective diameter.

9. The external ultrasonic probe according to claim 1, wherein the multiple transducers of the transducer array are arrayed only in the first direction; and an acoustic effective diameter in the second direction is 6 to 12 mm.

10. The external ultrasonic probe according to claim 1, wherein the multiple transducers of the transducer array are arrayed in the first direction and in the second direction; and a maximum acoustic effective diameter in the second direction is 6 to 12 mm.

11. The external ultrasonic probe according to claim 1, wherein the multiple transducers generate ultrasonic waves having a central frequency of generated ultrasonic waves at 3 to 5 MHz; and a thickness on a center axis of the covering material is at 1.5 to 3 times a wavelength of the ultrasonic waves leaving the transducer array in the covering material.

* * * * *